(12) United States Patent
Chang

(10) Patent No.: US 6,743,191 B1
(45) Date of Patent: Jun. 1, 2004

(54) SUBSTITUTION INFUSION FLUID AND CITRATE ANTICOAGULATION

(75) Inventor: Pe Chou Chang, Leiden (NL)

(73) Assignee: Edwards Lifesciences AG, St-Prex (CH)

( * ) Notice: Subject to any disclaimer, the term of this patent is extended or adjusted under 35 U.S.C. 154(b) by 0 days.

(21) Appl. No.: 09/959,543

(22) PCT Filed: Apr. 20, 2000

(86) PCT No.: PCT/EP00/03583

§ 371 (c)(1),
(2), (4) Date: Oct. 23, 2001

(87) PCT Pub. No.: WO00/64456

PCT Pub. Date: Nov. 2, 2000

(30) Foreign Application Priority Data

Apr. 26, 1999 (EP) .............................. 99201302

(51) Int. Cl.⁷ .................. A61M 1/34; A61K 33/00; A01N 1/02
(52) U.S. Cl. ............. 604/4.01; 210/646; 210/647; 210/650; 424/601; 424/630; 424/639; 424/646; 424/663; 424/682; 424/717; 514/822; 604/5.01; 604/6.07; 604/6.09
(58) Field of Search ................ 210/645, 646, 210/647, 650; 424/601, 630, 639, 646, 663, 682, 717, 603; 514/822; 604/4.01, 5.01, 6.07, 6.09

(56) References Cited

U.S. PATENT DOCUMENTS

| | | |
|---|---|---|
| 4,308,255 A | 12/1981 | Raj et al. |
| 4,336,881 A | 6/1982 | Babb et al. |
| 4,339,433 A | 7/1982 | Kartinos et al. |
| 4,489,535 A | 12/1984 | Veltman |
| 4,574,085 A | 3/1986 | Dolkart et al. |
| 4,604,379 A | 8/1986 | Twardowski et al. |
| 4,663,166 A | 5/1987 | Veech |

(List continued on next page.)

FOREIGN PATENT DOCUMENTS

| | | |
|---|---|---|
| DE | 3224823 A1 | 1/1984 |
| DE | 4122754 A1 | 1/1993 |

(List continued on next page.)

OTHER PUBLICATIONS

Ashton, D.N., et al.; "Recent advances in continuous renal replacement therapy: citrate anticoagulated continuous arteriovenous hemodialysis"; ANNA Journal, (1991 Jun.); 18 (3) 263–7, 329; XP000978120; Abstract, p. 265.

(List continued on next page.)

*Primary Examiner*—John Kim
(74) *Attorney, Agent, or Firm*—Lena I. Vinitskaya; Louis Cullman

(57) ABSTRACT

The invention relates to a substitution infusion fluid for hemofiltration of a specific composition. The use of said substitution infusion fluid significantly reduces the risk of the occurrence of abnormalities in a patient undergoing pure hemofiltration. The invention also relates to process for pure hemofiltration of blood wherein said substitution infusion fluid is used. The invention also relates to a matching citrate anticoagulation fluid of a specific composition. The invention also relates to a process for pure hemofiltration of blood wherein said substitution infusion fluid is used in combination with said citrate anticoagulation fluid. The use of said substitution infusion fluid in combination with said citrate anticoagulation fluid significantly further reduces the risk of the occurrence of abnormalities in a patient undergoing pure hemofiltration.

27 Claims, 1 Drawing Sheet

U.S. PATENT DOCUMENTS

| | | |
|---|---|---|
| 4,690,772 A | 9/1987 | Tell et al. |
| 4,879,280 A | 11/1989 | Seyffart et al. |
| 4,880,629 A | 11/1989 | Okamoto et al. |
| 4,886,789 A | 12/1989 | Milner |
| 4,889,634 A | 12/1989 | El-Rashidy |
| 4,980,374 A | 12/1990 | Steudle et al. |
| 5,011,826 A | 4/1991 | Steudle et al. |
| 5,032,615 A * | 7/1991 | Ward et al. ............... 514/574 |
| 5,192,459 A | 3/1993 | Tell et al. |
| 5,211,643 A | 5/1993 | Reinhardt et al. |
| 5,252,213 A | 10/1993 | Ahmad et al. |
| 5,296,242 A | 3/1994 | Zander |
| 5,436,232 A | 7/1995 | Forster et al. |
| 5,589,197 A | 12/1996 | Shockley et al. |
| 5,597,805 A | 1/1997 | Breborowicz et al. |
| 5,616,248 A | 4/1997 | Schal |
| 5,629,025 A | 5/1997 | Shockley et al. |
| 5,631,025 A | 5/1997 | Shockley et al. |
| 5,670,176 A | 9/1997 | Martis et al. |
| 5,698,230 A | 12/1997 | Martis et al. |
| 5,827,820 A | 10/1998 | duMoulin et al. |
| 5,945,129 A | 8/1999 | Knerr et al. |
| 5,945,449 A | 8/1999 | Purcell et al. |
| 5,955,257 A * | 9/1999 | Burger et al. ............... 435/2 |
| 5,955,450 A | 9/1999 | Breborowicz et al. |
| 6,017,942 A * | 1/2000 | Bergstrom ............... 514/399 |
| 6,020,007 A | 2/2000 | Veech |
| 6,077,836 A | 6/2000 | Milner |
| 6,083,935 A | 7/2000 | Wu et al. |
| 6,156,797 A | 12/2000 | Kubo et al. |
| 6,214,802 B1 | 4/2001 | Nakamura et al. |
| 6,248,726 B1 | 6/2001 | Alsop et al. |
| 6,251,437 B1 | 6/2001 | Fischbach |
| 6,277,556 B1 * | 8/2001 | Grode et al. ............... 435/2 |
| 6,277,815 B1 | 8/2001 | Knerr |
| 6,306,836 B1 | 10/2001 | Martis et al. |
| 6,309,673 B1 | 10/2001 | Duponchelle et al. |
| 2001/0003794 A1 | 6/2001 | Landry et al. |

FOREIGN PATENT DOCUMENTS

| | | |
|---|---|---|
| DE | 4211456 C1 | 12/1993 |
| EP | 76355 A2 | 4/1983 |
| EP | 86553 A1 | 8/1983 |
| EP | 115911 A1 | 8/1984 |
| EP | 153164 A2 | 8/1985 |
| EP | 399918 A2 | 11/1990 |
| EP | 456928 A1 | 11/1991 |
| EP | 602014 A1 | 6/1994 |
| EP | 821951 A1 | 2/1998 |
| GB | 2084484 A | 4/1982 |
| JP | 3 56010109 A | 2/1981 |
| JP | 56 128711 A | 10/1981 |
| JP | 01 242531 A | 9/1989 |
| JP | 4 03038527 A | 2/1991 |
| JP | 04 069341 A | 3/1992 |
| JP | 4 05105633 A | 4/1993 |
| JP | 4 06105906 A | 4/1994 |
| JP | 4 06178802 A | 6/1994 |
| JP | 4 06237991 A | 8/1994 |
| JP | 4 06245995 A | 9/1994 |
| JP | 4 06335527 A | 12/1994 |
| JP | 4 06335528 A | 12/1994 |
| JP | 4 07059846 A | 3/1995 |
| JP | 4 08092071 A | 4/1996 |
| JP | 4 08131542 A | 5/1996 |
| JP | 4 08164199 A | 6/1996 |
| JP | 4 08169836 A | 7/1996 |
| JP | 4 10087478 A | 4/1998 |
| JP | 4 11114054 A | 4/1999 |
| JP | 4 11197240 A | 7/1999 |
| JP | 4 11343230 A | 12/1999 |
| JP | 0 2000037452 A | 2/2000 |
| JP | 0 2000051348 A | 2/2000 |
| JP | 0 2000072658 A | 3/2000 |
| JP | 0 2000140095 A | 5/2000 |
| JP | 0 2000245826 A | 9/2000 |
| JP | 0 2000288083 A | 10/2000 |
| JP | 0 2001054570 A | 2/2001 |
| WO | WO 90/15612 A | 12/1990 |
| WO | WO 91/10457 A1 | 7/1991 |
| WO | WO 93/19792 A1 | 10/1993 |
| WO | WO 93/24108 A1 | 12/1993 |
| WO | WO 96/01118 A1 | 1/1996 |
| WO | WO 97/30694 A1 | 8/1997 |
| WO | WO 98/10745 A1 | 3/1998 |
| WO | WO 98/29151 A1 | 7/1998 |
| WO | WO 99/01144 A1 | 1/1999 |
| WO | WO 99/09953 A1 | 3/1999 |
| WO | WO 99/17762 A1 | 4/1999 |
| WO | WO 99/20249 A1 | 4/1999 |
| WO | WO 00/33853 A | 6/2000 |

OTHER PUBLICATIONS

Macias, W.L.; "Choice of replacement fluid/dialysate anion in continuous renal replacement therapy"; American Journal of Kidney Diseases, (1996) 28/5 Suppl. 3 (S15–S20); XP000978102; Abstract; p. S15–p. S16; p. S19.

Palsson, R., et al.; "Regional citrate anticoagulation in continuous venovenous hemofiltration in critically ill patients with a high risk of bleeding"; Kidney International, (1999 May) 55 (5); 1991–7; XP000978115; Abstract.

Sieberth, H.G,; ["Composition of the rinsing water for extracorporeal hemodialysis in acute and chronic renal failure"]; Zusammensetzung des Waschwassers fur die extracorporate Hamodialyse der akuten und chronischen Niereninsufflzienz; Medizinische Technik, (1974) 94/2 (28–32); Coden: Meteav, XP000856013; Abstract; p. 31, col. 2; Table 1.

Van Stone, J.C.; "Individualization of the dialysate prescription in chronic hemodialysis"; Dialysis and Transplantation, (1994) 23/11 (624–625+628–635); XP000856008; Abstract the Whole Document, p. 634.

* cited by examiner

US 6,743,191 B1

SUBSTITUTION INFUSION FLUID AND CITRATE ANTICOAGULATION

TECHNICAL FIELD

The invention relates to a substitution infusion fluid, particularly for use in pure, continuous-veno-venous hemofiltration of blood using citrate as anticoagulant and to a matching citrate anticoagulation solution particularly for use in pure, continuous-veno-venous hemofiltration of blood.

BACKGROUND ART

Pure hemofiltration is a renal-replacement therapy that is widely used in Intensive Care Units (ICU's) for critically ill patients with acute renal failure. In ICU's, pure hemofiltration therapy is mostly employed as so-called continuous-veno-venous hemofiltration (CVVH) and to a much lesser extent as continuous-arterio-venous-hemofiltration (CAVH).

Another for of renal replacement therapy that can be used for patients with renal failure in ICU's is hemodialysis. Pure hemofiltration as a renal-replacement therapy in an ICU can also be combined with hemodialysis as so-called continuous-veno-venous-hemodiafiltration (usually abbreviated as CVVHD or CVVHDF) or as continuous-arterio-venous-hemodiafiltration (usually abbreviated as CAVHD or CAVHDF). The addition of hemodialysis to a hemofiltration therapy implies the addition of a hemodialysis fluid (a so-called 'dialysate') flow, making such combined therapy forms more complex than pure hemofiltration. Hemodialysis usually can only be applied for a few hours per day and is much less effective than pure hemofiltration. With hemodialysis usually only small amounts of plasma fluid can be removed per hour of treatment.

Typically, in CVVH, CAVH, CVVHD, CAVHD, and hemodialysis an artificial kidney is used. This kidney may be formed of hollow-fibers or of plates, and is connected to a patients bloodstream by an extracorporeal circuit. In CVVH (D) the supply from and return to the blood of the patient is made via two venous accesses, using a blood pump to provide the driving force for the transport of blood from the patient into the artificial kidney and back to the patient. In CAVH(D), the access which provides the supply of blood to the artificial kidney is made via an artery and the return of the blood to the patient is made via a venous access. In this set-up no blood pump is used, because the arterial blood pressure is used to provide the driving force for the transport of blood, which implies that the blood flow rate directly varies with the blood pressure. Because of better control of blood flow, no risk of arterial catheter-related complications, and higher treatment efficiency, CVVH is preferred above CAVH as renal replacement therapy in ICU's.

In CVVH the patient's blood is passed through the artificial kidney, over a semipermeable membrane. The semipermeable membrane selectively allows plasma water and matter in the blood to cross the membrane from the blood compartment into the filtrate compartment, mimicking the natural filtering function of a kidney. This leads to a considerable loss of fluid from the blood, which is removed as the filtrate in the artificial kidney. Every liter of filtrate fluid that is removed in the artificial kidney, contains a large fraction of the molecules that are dissolved in the plasma, like urea, creatinine, phosphate, potassium, sodium, glucose, amino acids, water-soluble vitamins, and trace elements. The fraction of the molecules that passes the semipermeable membrane depends mainly on the physico-chemical characteristics of the molecules and the membrane. In order to keep the blood volume of the patient at a desired (constant) level, a substitution infusion fluid is added to the blood stream in the extracorporeal circuit, after is has passed through the artificial kidney and before it re-enters the patient's vein.

In a normal CVVH procedure, approximately 50 liters of filtrate are removed per 24 hours, and approximately the same amount of substitution infusion fluid is added into the return of blood side of the extracorporeal circuit. The substitution Infusion fluid commonly used is conventional infusion fluid consisting of a physiological saline solution generally only containing about 140 mmol/L of sodium ions, 1,6 mmol/L of calcium ions, 0.75 mmol/L of magnesium ions, 36 mmol/L of bicarbonate ions, and 110 mmol/L of chloride ions. All forms of hemodialysis or hemodiafiltration therapies are characteristically different from pure hemofiltration by the use of a dialysate fluid flow along the semipermeable membrane side opposite to the blood side. The removal of molecules (clearance) in hemodialysis is dependent on the diffusion of molecules through the semipermeable membrane, while in hemofiltration the molecules are removed by convection. Therefore, all hemodialysis forms of treatment are much less effective in removing larger molecules than pure hemofiltration.

In order to prevent coagulation of the blood during hemofiltration, usually an anticoagulant is added to the blood in the extracorporeal circuit before it enters the artificial kidney. In the past, heparin or fractionated heparin was often used for this purpose. A drawback of the use of heparin, however, is that this use leads to systemic anticoagulation (i.e., anticoagulation of all blood including that within the patient), giving rise to the risk of the occurrence of serious bleeding complications, particularly in seriously ill patients.

Instead of heparin, citrate ions can be used as anticoagulant, as has been proposed for the first time by Pinnick et al., New England Journal of Medicine 1983, 308, 258–263, for hemodialysis. Citrate ions, usually added in the form of trisodium citrate, are believed to bind free calcium ions In the blood, which have a pivotal role in the coagulation cascade.

Citrate ions, added to the blood into the extracorporeal circuit before it enters the artificial kidney, are only active as an anticoagulant in the extracorporeal circuit, whereby the risk of bleeding complications due to systemic anticoagulation is avoided. When citrate ions are applied during hemodialysis forms of treatment, a calcium-and magnesium-free dialysate is required. Therefore, the application of citrate ions during hemodialysis is more complex than during pure hemofiltration.

Citrate ions are mainly metabolised in skeletal muscle and liver tissue. Only in cases of severe hepatic failure combined with severe shock, or of certain (rare) metabolic diseases, the metabolism of citrate may run short leading to too high citrate concentrations in the systemic blood circulation, which on its turn may endanger the patient. Accordingly, citrate ions are an attractive anticoagulant for use in pure hemofiltration procedures, especially for use in CVVH treatment in ICU patients.

During hemofiltration, part of the citrate ions is removed from the blood in the artificial kidney. The citrate ions that flow over into the systemic circulation of the patient, are rapidly metabolised to bicarbonate ions in skeletal muscle and liver tissue (about 2.8 molecules bicarbonate are made from 1 citrate molecule). Because trisodium citrate contains on a molar basis three times as many sodium ions as citrate ions, the sodium ions that flow over into the systemic circulation of the patient significantly increases the blood sodium concentration. As a result hypernatremia and/or an abnormal increase in bicarbonate ions (metabolic alkalosis) may occur. Therefore, replacement of a part of the trisodium citrate by citric acid may reduce the sodium load and, by its acid component, neutralizes part of the bicarbonate generated. Accordingly, a mixture of trisodium citrate with citric acid, is a more attractive anticoagulant for use in hemofiltration procedures than trisodium citrate alone, especially for use in CVVH treatment in ICU patients. The exact concentrations of the mixture of trisodium citrate with citric acid is important because too much citric acid will induce acidosis in the patient and when the concentration of the components are too high or too low, the volume that needs to be infused into the extracorporeal circuit either becomes too small to infuse precisely or becomes a too high volume load for the patient. There are several reasons why the use of citrate as anticoagulant during pure, continuous-venovenous hemofiltration of blood makes it necessary to use a matching substitution fluid and vice versa. The clearance of dissolved molecules from the blood by the pure hemofiltration process is influenced by the use of citrate. Further, the citric acid component, the bicarbonate that is generated from the citrate molecules that flow over into the systemic circulation, and the sodium concentration of the citrate mixture all determine the amount of sodium, calcium, phosphate, and some other components in the substitution fluid that needs to be given to the patient in order to prevent complications from occurring.

Because citrate ions bind to positively charged metal ions like calcium, magnesium, iron, zinc, copper, and manganese, these ions are also partly removed in the artificial kidney, leading to a net removal of calcium and magnesium ions and other metal ions from the patient's blood. As a result, hypocalcemia and/or hypomagnesemia and/or shortages of other metal ions may be induced in the patient. Especially the hypocalcemia, hypomagnesemia, and/or metabolic alkalosis, may induce life-threatening complications in the patient.

The process of hemofiltration, induces a net removal of phosphate and potassium ions, trace elements, water-soluble vitamins, amino acids and of glucose in the artificial kidney. For example, when during CVVH 50 liters of plasma filtrate per day are removed, it usually contains all of the dissolved urea, creatinine, sodium, potassium, and bicarbonate, and significant amounts of the other dissolved molecules like phosphate and calcium salts. This may lead to significant degrees of hypovolemia, hypophosphatemia, hypokalemia, and shortages of trace elements, water-soluble vitamins, amino acids, and/or glucose, with the risk of deteriorating the patient's condition. Especially the hypophosphatemia may also induce life-threatening complications in the patient. In order to prevent these complications from occurring, it is crucial to return an appropriate volume of substitution infusion fluid per unit of time, containing appropriate amounts of the removed molecules that are needed by the patient.

DISCLOSURE OF THE INVENTION

The present invention aims at providing a means of preventing the occurrence of the above described abnormalities, and thereby to overcome the problems encountered during pure hemofiltration in the past. It is especially an object of the invention to obviate the shortcomings of the pure, continuous-veno-venous-hemofiltration procedure followed in ICU's up till now, particularly when citrate ions are used as anticoagulant.

Surprisingly, it has been found that these goals may be reached by making use of a substitution infusion fluid of a specific composition. Accordingly, the invention relates to an aqueous substitution infusion fluid for hemofiltration comprising between 0.2 and 1, preferably between 0.5 and 0.9 mmol/L of dihydrogen phosphate ions;

between 70 and 130, preferably between 100 and 120 mmol/L of sodium ions;

between 1.6 and 2.6, preferably between 1.9 and 2.4 mmol/L of calcium ions;

between 0.25 and 1.25, preferably between 0.5 and 1.0 mmol/L of magnesium ions;

between 1 and 4, preferably between 1.8 and 3.5 mmol/L of potassium ions;

between 3 and 11.5, preferably between 5.5. and 7.5 mmol/L of glucose;

below 5.5 mmol/L, preferably between 0 and 3.1 mmol/L of acetate ions; and below 5.5. mmol/L, preferably between 0 and 3.1 mmol/L of bicarbonate ions.

The substitution infusion fluid is usually supplemented with chloride ions to achieve a neutral electrochemical balance.

By using the specific substitution infusion fluid together with a matching citrate anticoagulant solution that is described further and according to the invention in a hemofiltration procedure, the concentrations of potassium, phosphate, calcium, magnesium, bicarbonate ions, and of glucose remain substantially within ranges of which it is accepted that they lead not to unacceptable risk of complications within the patient. In most cases, the concentrations of these ions and glucose remain more or less constant in the systemic blood of the patient undergoing hemofiltration. Consequently, the chances of the occurrence of the problems encountered in hemofiltration to date are significantly reduced, if not eliminated altogether. Particularly, the chances of the above indicated abnormalities, such as electrolyte or acid-base abnormalities are significantly reduced.

The substitution infusion fluid according to the invention may conveniently be prepared by dissolving salts in water in such amounts that the desired concentrations are reached, as is well within the expertise of the normal person skilled in the art. During the preparation, it is desired that a sterile environment is maintained. Accordingly, the substitution infusion fluid preferably is sterile, according to the European pharmacopeia, thereby avoiding the risk of infections in a patient when the fluid is used during hemofiltration.

Typically, the substitution infusion fluid is hypotonic. Exemplary values are between 200 and 270 mOsm/L. Nevertheless, it has been found that the fluid is well tolerated by patients when it is used in a hemofiltration procedure. It has been found that the hypotonicity is in fact beneficial by compensating for the hypertonicity induced at the arterial side of the extracorporeal circuit by the anticoagulant. The result is that the blood that is returned into the patient's blood stream has substantially normal (physiological) osmolarity.

Surprisingly, it has also been found that the prevention of the occurrence of the above described abnormalities may further be improved by making use of a matching citrate anticoagulation fluid of a specific composition. Accordingly, the invention also relates to an aqueous citrate anticoagulation fluid for pure, continuous-veno-venous-hemofiltration comprising between 19 and 135 mmol/L of ctric acid; and between 80 and 550 mmol/L of trisodium citrate, preferably between 106 and 290 mmol/L of trisodium citrate.

By using the specific citrate anticoagulation infusion fluid according to the invention in a pure, continuous-veno-venous-hemofiltration procedure, the blood is effectively anticoagulated within the extracorporeal circuit and not within the systemic circulation of the patient and the concentrations of sodium, calcium, magnesium, and bicarbonate ions remain substantially within ranges of which it is accepted that they lead not to unacceptable risk of complications within the patient. In most cases, the concentrations of these ions remain more or less constant in the systemic blood of the patient undergoing hemofiltration. Consequently, the chances of the occurrence of the problems encountered to date in pure hemofiltration with citrate as anticoagulant are significantly reduced, if not eliminated altogether. Particularly, the chances of the above indicated abnormalities, such as electrolyte or acid-base abnormalities, and/or severe bleeding complications are significantly reduced.

The specific citrate anticoagulation infusion fluid according to the invention may conveniently be prepared by dissolving trisodium citrate and citric acid in water in such amounts that the desired concentrations are reached, as is well within the expertise of the normal person skilled in the art. During the preparation, it is desired that a sterile environment is maintained. Accordingly, the citrate anticoagulation infusion fluid preferably is sterile, according to the European pharmacopeia, thereby avoiding the risk of infections in a patient when the fluid is used during pure hemofiltration. This citrate anticoagulant solution is preferably used during pure, continuous-veno-venous-hemofiltration in combination with a matching substitution infusion fluid out of the above mentioned ranges, comprising about 118 mmol/L of sodium ions, about 2.3 mmol/L of calcium ions, about 2.6 mmol/L of potassium ions, about 0.8 mmol/L of phosphate ions, about 0.9 mmol/L of magnesium ions, about 6.5 mmol/L of glucose, less than 5.5 mmol/L of acetic acid, and chloride ions to keep electrochemical balance.

The addition of acetic acid may help to prevent the formation of calciumphosphate sedimentation in said solutions.

BEST MODE FOR CARRYING OUT THE INVENTION

In a preferred embodiment, the present substitution infusion fluid is an aqueous solution meeting the above requirements, preferably comprising about 107 mmol/L of sodium ions, about 2.5 mmol/L of potassium ions, about 0.83 mmol/L of phosphate ions, about 2.3 mmol/L of calcium ions, about 0.89 mmol/L of magnesium ions, about 6.4 mmol/L of glucose, and less than 3.1 mmol/L of acetate ions, in the absence of bicarbonate ions, and supplemented with chloride ions to keep electrochemical balance. It has been found that when a substitution infusion fluid of this type is used in combination with a matching solution of trisodium citrate consisting of 500 mmol/L trisodium citrate as an anticoagulant, the concentrations of the indicated ions in the patient's blood remain substantially within the physiological range throughout the pure hemofiltration procedure.

In a preferred embodiment, the present citrate anticoagulation solution for pure hemofiltration treatment is an aqueous solution meeting the above requirements, comprising about 38 mmol/L of citric acid and about 212 mmol/L of trisodium citrate. This citrate anticoagulation solution is preferably used during pure, continuous-veno-venous-hemofiltration in combination with a matching substitution infusion fluid comprising about 118 mmol/L of sodium ions, about 2.3 mmol/L of calcium ions, about 2.6 mmol/L of potassium ions, about 0.8 mmol/L of phosphate ions, about 0.9 mmol/L of magnesium ions, about 6.5 mmol/L of glucose, less than 5.5 mmol/L of acetic acid, and chloride ions to keep electrochemical balance.

BRIEF DESCRIPTION OF DRAWING

By way of example, the invention will now be described in more detail while referring to the enclosed FIGURE, which illustrates the process of hemofiltration by CVVH.

Blood is extracted from a vein of a patient and transported to an artificial kidney (4, 5, 6) via the arterial side (1) of an extracorporeal circuit (1, 2) by the driving force of a blood pump (14). Anticoagulant, a matching citrate solution, is added to the blood between the blood pump and the artificial kidney (10).

Figure 1:
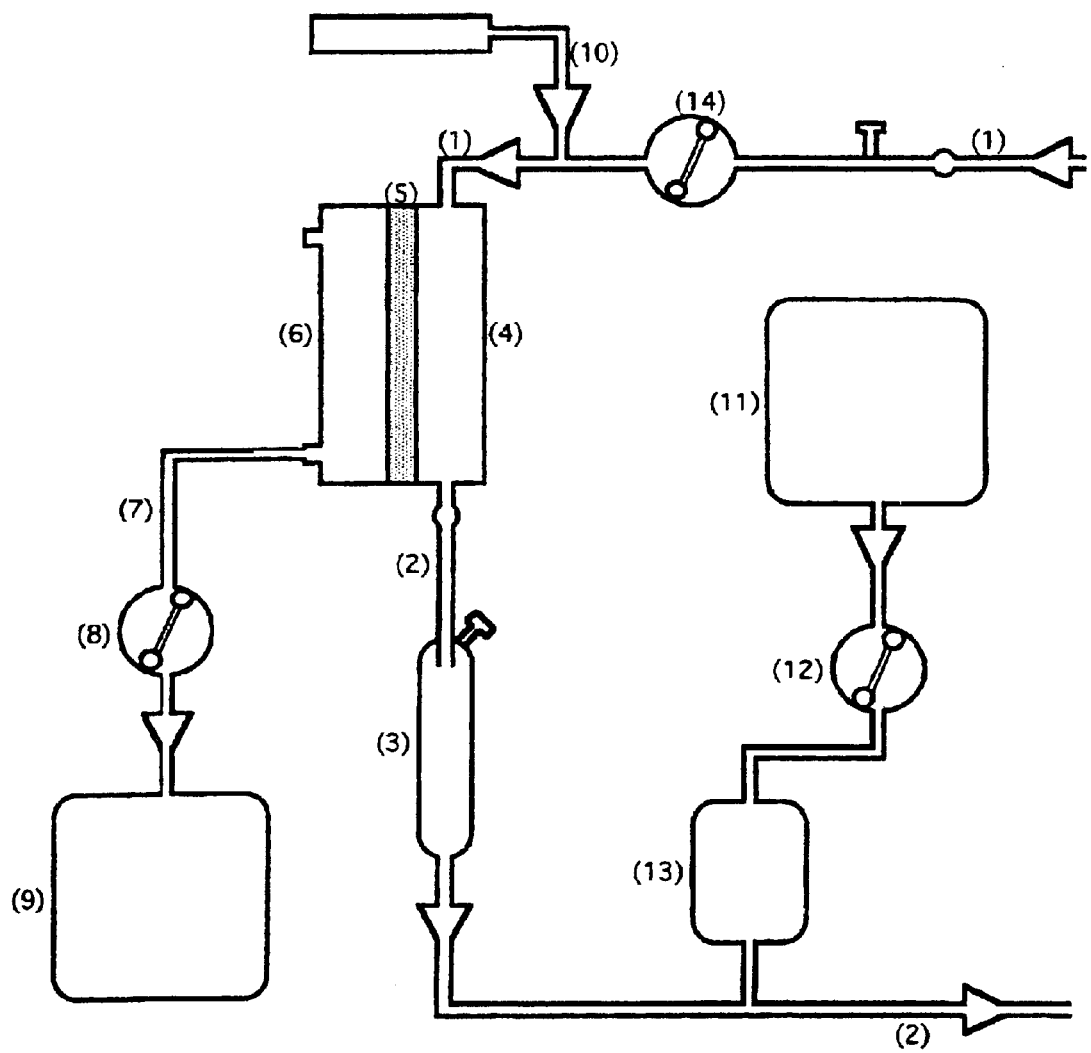

In the artificial kidney, the blood is filtered over a semipermeable membrane (5). The filtrate is removed from the fitrate compartment of the artificial kidney (6) via connecting tubing (7). A pump (8) takes care of the transport of filtrate into a collection reservoir (9).

The retentate blood is transported back from the retentate compartment of the artificial kidney (4) to the patient's blood stream via the venous side (return side) of the extracorporeal circuit (2), after passage of an airtrap (3). The airtrap serves to remove all air bubbles from the blood before it is returned into the patent's blood stream. Preferably, the blood is returned into the patient's blood stream at the same place as at which it was extracted, e.g., by way of a double-lumen venous catheter.

Before the hemofiltered blood is returned to the patient, the substitution infusion fluid is added from a reservoir (11), via a pump (12) and a heater (13). The heater ensures that the fluid ultimately entering the patient's body is substantially equal to the patient's body temperature, thus making the entire procedure substantially less uncomfortable.

During the procedure, the amount of filtrate collected in the reservoir (9) is determined accurately, e.g., by weighing (device not shown). The amount of substitution infusion fluid added to the blood is adapted to this amount. This makes it possible to make sure that an exactly predetermined volume of fluid is returned to the patient's body (2), matching the originally extracted volume therefrom or adapted to the fluid balance needed in a particular patient (1). The flow through pumps (8) and (12) are accordingly precisely adjusted to one another. Typically, the substitution infusion fluid is administered (infused) into the blood at a rate of between 8 and 80 mL per 200 mL blood. In practice, means, such as an audible alarm, are often provided for alarming nursing personnel should an interruption of the blood, filtrate, or substitution flow occur. Typically, said specific anticoagulation fluid of trisodium citrate and citric add is infused into the blood at a rate of between 1.3 and 4 mL per 200 mL blood.

What is claimed is:

1. An a queous substitution infusion fluid for pure hemofiltration of blood using citrate as anticoagulant comprising:
   between 0.2 and 1 mmol/L of dihydrogen phosphate ions;
   between 70 and 130 mmol/L of sodium ions;
   between 1.6 and 2.6 mmol/L of calcium ions;
   between 0.25 and 1.25 mmol/L of magnesium ions;
   between 1 and 4 mmol/L of potassium ions;
   between 3 and 11.5 mmol/L of glucose;
   below 5.5 mmol/L of acetate ions; and
   chloride ions to keep electrochemical balance.

2. The substitution infusion fluid according to claim 1, comprising between 0.4 and 0.8 mmol/L of dihydrogen phosphate ions.

3. The substitution infusion fluid according to claim 1 comprising between 90 and 110 mmol/L of sodium ions.

4. The substitution infusion fluid according to claim 1 comprising between 1.9 and 2.3 mmol/L of calcium ions.

5. The substitution infusion fluid according to claim 1 comprising between 0.5 and 1 mmol/L of magnesium ions.

6. The substitution infusion fluid according to claim 1 comprising between 1.8 and 3.5 mmol/L of potassium ions.

7. The substitution infusion fluid according to claim 1 comprising between 5.5 and 7.5 mmol/L of glucose.

8. The substitution infusion fluid according to claim 1 comprising between 0 and 3.1 mmol/L of acetate ions.

9. The substitution infusion fluid according to claim 1 comprising between 0 and 3.1 mmol/L of bicarbonate ions.

10. The substitution infusion fluid according to claim 1 comprising amino acids and/or trace elements.

11. An aqueous substitution infusion fluid for pure hemofiltration of blood using citrate as anticoagulant comprising about 100 mmol/L of sodium ions, about 2.1 mmol/L of calcium ions, about 2.2 mmol/L of potassium ions, about 0.6 mmol/L of phosphate ions, about 0.8 mmol/L of magnesium ions, about 7.0 mmol/L of glucose, less than 3.1 mmol/L of acetate ions, and chloride ions to keep electrochemical balance.

12. An aqueous substitution infusion fluid for pure hemofiltration of blood using citrate as anticoagulant comprising about 107 mmol/L of sodium ions, about 2.3 mmol/L of calcium ions, about 2.5 mol/L of potassium ions, about 0.8 mmol/L of phosphate ions, about 0.9 mmol/L of magnesium ions, about 6.4 mmol/L of glucose, less than 5.5 mmol/L of acetic acid, and chloride ions to keep electrochemical balance.

13. An aqueous substitution infusion fluid for pure hemofiltration of blood using citrate as anticoagulant comprising about 118 mmol/L of sodium ions, about 2.3 mmol/L of calcium ions, about 2.6 mmol/L of potassium ions, about 0.8 mmol/L of phosphate ions, about 0.9 mmol/L of magnesium ions, about 6.5 mmol/L of glucose, less than 5.5 mmol/L of acetic acid, and chloride ions to keep electrochemical balance.

14. The substitution infusion fluid for pure hemofiltration according to claim 1 further comprising iron ions, and/or zinc ions, and/or copper ions, and/or manganese ions, and/or water-soluble vitamins.

15. The substitution infusion fluid for pure hemofiltration according to claim 1 further comprising between 0.5 and 5.5 mmol/L of acetic acid.

16. The substitution infusion fluid for pure hemofiltration according to claim 1 further comprising a matching citrate anticoagulation solution comprising between 19 and 135 mmol/L of citric acid and between 106 and 290 mmol/L of trisodium citrate.

17. A citrate anticoagulation solution for anticoagulation of circulating blood during pure hemofiltration, comprising between 19 and 135 mmol/L of citric acid and between 106 and 290 mmol/L of trisodium citrate.

18. A citrate anticoagulation solution for anticoagulation during pure hemofiltration of blood being an aqueous solution comprising about 38 mmol/L of citric acid and about 212 mmol/L of trisodium citrate.

19. A pure hemofiltration process for blood comprising:
   a) providing blood to an artificial kidney via an extracorpeal circuit;
   b) adding a citrate/citric acid anticoagulant to the blood prior to entering the artificial kidney;
   c) filtering the blood using a semi-permeable membrane;
   d) adding a hemofiltration substitution fluid according to claim 1 back to the filtered blood;
   e) returning the filtered blood containing the substitution fluid back to the patient; and
   wherein said anticoagulant and said substitution fluid are matched to provide for consistent concentrations of systemic electrolytes in a patient undergoing hemofiltration.

20. The pure hemofiltration process according to claim 19 wherein said systemic electrolytes comprise the group consisting of chloride, sodium, potassium, phosphate, calcium, magnesium, bicarbonate and combinations thereof.

21. A kit for performing hemofiltration comprising:
   a citrate/citric acid anticoagulant composition and a matched substitution fluid according to claim 1 that provide for consistent concentrations of systemic electrolytes in a patient undergoing hemofiltration.

22. The kit according to claim 21 wherein said citrate/citric acid composition is provided in a substantially liquid form.

23. The kit according to claim 21 wherein said citrate/citric acid composition is provided in a substantially solid form.

24. The kit according to claim 21 wherein said substitution fluid is provided in a substantially liquid form.

25. The kit according to claim 21 wherein said substitution fluid is provided in a substantially solid form.

26. The according to claims 21 or 24 wherein said substitution fluid is hypotonic.

27. The according to claim 21 wherein said citric acid composition and 21 wherein said substitution fluid are sterile.

* * * * *

UNITED STATES PATENT AND TRADEMARK OFFICE
CERTIFICATE OF CORRECTION

| | | |
|---|---|---|
| PATENT NO. | : 6,743,191 B1 | Page 1 of 2 |
| APPLICATION NO. | : 09/959543 | |
| DATED | : June 1, 2004 | |
| INVENTOR(S) | : Pe Chou Chang | |

It is certified that error appears in the above-identified patent and that said Letters Patent is hereby corrected as shown below:

IN THE SPECIFICATION:

In Column 1, Line 38, before "bloodstream" please delete "patients" and insert --patient's.--

In Column 2, Line 10, after "substitution" please delete "Infusion" and insert --infusion.--

In Column 2, Line 40, after "ions" please delete "In" and insert --in.--

In Column 3, Line 3, after "As a result" please delete "hypematremia" and insert --hypernatremia.--

In Column 4, Line 65, after "135 mmol/L of" please delete "ctric" and insert --citric.--

In Column 6, Line 52, after "citrate and citric" please delete "add" and insert --acid.--

IN THE CLAIMS:

In Column 6, Line 56, Claim 1, before "substitution" please delete "An a queous" and insert --An aqueous.--

In Column 7, Line 19, Claim 10, before "comprising" please insert --further.--

In Column 7, Line 31, Claim 12, after "about 2.5" please delete "mol/L" and insert --mmol/L.--

In Column 8, Line 46, Claim 26, before "according" please insert --kit.--

UNITED STATES PATENT AND TRADEMARK OFFICE
CERTIFICATE OF CORRECTION

PATENT NO. : 6,743,191 B1
APPLICATION NO. : 09/959543
DATED : June 1, 2004
INVENTOR(S) : Pe Chou Chang It is certified that error appears in the above-identified patent and that said Letters Patent is hereby corrected as shown below:

In Column 8, Line 48, Claim 27, please delete the entire sentence and replace with --The kit according to claim 21 wherein said citric acid composition and said substitution fluid are sterile.--

Signed and Sealed this

Fifth Day of June, 2007

JON W. DUDAS
*Director of the United States Patent and Trademark Office*